United States Patent
Xu et al.

(10) Patent No.: US 8,962,017 B2
(45) Date of Patent: *Feb. 24, 2015

(54) FORMULATION OF SILYMARIN WITH HIGH EFFICACY AND PROLONGED ACTION AND THE PREPARATION METHOD THEREOF

(75) Inventors: Ximing Xu, Jiangsu (CN); Jiangnan Yu, Jiangsu (CN); Shanshan Tong, Jiangsu (CN); Yuan Zhu, Jiangsu (CN); Xia Cao, Jiangsu (CN)

(73) Assignee: Jiangsu University (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/126,071

(22) PCT Filed: Nov. 23, 2009

(86) PCT No.: PCT/CN2009/001298
§ 371 (c)(1),
(2), (4) Date: Apr. 26, 2011

(87) PCT Pub. No.: WO2010/075663
PCT Pub. Date: Jul. 8, 2010

(65) Prior Publication Data
US 2011/0201680 A1 Aug. 18, 2011

(30) Foreign Application Priority Data
Dec. 31, 2008 (CN) .......................... 2008 1 0242988

(51) Int. Cl.
*A61K 31/353* (2006.01)
*A61P 1/00* (2006.01)
(Continued)

(52) U.S. Cl.
CPC ............... *A61K 31/357* (2013.01); *A61K 9/146* (2013.01); *A61K 9/5115* (2013.01);
(Continued)

(58) Field of Classification Search
None
See application file for complete search history.

(56) References Cited

U.S. PATENT DOCUMENTS

2003/0069302 A1 * 4/2003 Zielinski ................... 514/452
2005/0064034 A1 * 3/2005 Li et al. ..................... 424/469
(Continued)

FOREIGN PATENT DOCUMENTS

CN 101164537 A * 4/2008
EP 1499895 B1 * 5/2008

OTHER PUBLICATIONS

Li et al., Controlled release of avermectin from porous hollow silica nanoparticles: Influence of shell thickness on loading efficiency, UV-shielding property and release, Journal of Controlled Release, 111 (2006) 81-88.*

(Continued)

*Primary Examiner* — Rachael E Bredefeld
*Assistant Examiner* — Dominic Lazaro
(74) *Attorney, Agent, or Firm* — Schmeiser, Olsen & Watts, LLP

(57) ABSTRACT

A high-efficacy, long-acting formulation of silymarin, comprising silymarin solid dispersion, silymarin-loaded silica nanoparticles, slow-release matrix material and release enhancer, wherein the mass ratio of these components is silymarin solid dispersion:silymarin-loaded silica nanoparticles:slow-release matrix material:release enhancer=1: 0.5~1.25:0.1~0.3:0.1~0.3; the drug loading rate of the said silymarin-loaded silica nanoparticles is 51.95%-52.87%; the said silymarin solid dispersion contains povidone K30, soybean lecithin and acrylic resin IV, and the mass ratio between silymarin and other medical accessories in silymarin solid dispersion is silymarin:povidone K30:soybean lecithin: acrylic resin IV=1:1~3:0.3~0.8:0.2~0.5. Compared with the existing formulations, the half life of the high-efficacy, long-acting formulation of silymarin disclosed in this invention is 2.3 times longer while the mean residence time (MRT) of which is 9.94 times longer; when tested in vivo in Beagle dogs, this new formulation of silymarin presents a smoother concentration-time curve and reaches a continuous release for 72 hours. This invention discloses its preparation method.

9 Claims, 2 Drawing Sheets

(51) Int. Cl.
  A61P 9/00      (2006.01)
  A61P 7/02      (2006.01)
  B29B 9/12      (2006.01)
  B82Y 5/00      (2011.01)
  A61K 31/357    (2006.01)
  A61K 9/14      (2006.01)
  A61K 9/51      (2006.01)
  A61K 47/02     (2006.01)
  A61K 47/24     (2006.01)
  A61K 47/30     (2006.01)
  A61K 47/32     (2006.01)

(52) U.S. Cl.
  CPC .............. *A61K 31/353* (2013.01); *A61K 47/02* (2013.01); *A61K 47/24* (2013.01); *A61K 47/30* (2013.01); *A61K 47/32* (2013.01); *Y10S 977/773* (2013.01); *Y10S 977/888* (2013.01); *Y10S 977/906* (2013.01)
  USPC .............. 424/457; 264/6; 424/400; 424/451; 424/464; 514/456; 549/362; 977/773; 977/888; 977/906

(56) References Cited

U.S. PATENT DOCUMENTS

2006/0057206 A1* 3/2006 Wong et al. ............ 424/473
2006/0068022 A1* 3/2006 Playford ............... 424/535

OTHER PUBLICATIONS

Scholfield, Composition of Soybean Lecithin, J. Am. Oil Chem. Soc., 58 (1981) 889-892.*

Abarkan et al., Tailored macro/microstructural properties of colloidal silica nanoparticles via microemulsion preparation, Polyhedron 25 (2006) 1763-1770.*

Huang et al., Single w/o microemulsion templating of CdS nanoparticles, J. Mater. Sci 39 (2004) 2411-2415.*

Zhu et al., Poly(L-lysine)-modified silica nanoparticles for the delivery of antisense oligonucleotides, Biotechnol. Appl. Biochem., 39 (2004) 179-187.*

Li et al., Fabrication of porous hollow silica nanoparticles and their applications in drug release control, J. Control. Release, 98 (2004) 245-254.*

Ke et al., Solubilities of Salicylic Acid in Supercritical Carbon Dioxide with Ethanol Cosolvent, J. Supercrit. Fluids, 1996, 9, 82-87.*

English language translation of CN 101164537.*

Li et al., Controlled release of avermectin from porous hollow silica nanoparticles: Influence of shell thickness on loading efficiency, UV-shielding property and release, Journal of Controlled Release, 111 (2006) 81-88 (Li II).*

Scholfield, Composition of Soybean Lecithin, J. Am. Oil Chem. Soc., 58 (1981) 889-892 (Scholfield).*

Abarkan et al., Tailored macro/microstructural properties of colloidal silica nanoparticles via microemulsion preparation, Polyhedron 25 (2006) 1763-1770 (Abarkan).*

Huang et al., Single w/o microemulsion templating of CdS nanoparticles, J. Mater. Sci 39 (2004) 2411-2415 (Huang).*

Zhu et al., Poly(L-lysine)-modified silica nanoparticles for the delivery of antisense oligonucleotides, Biotechnol. Appl. Biochem., 39 (2004) 179-187 (Zhu).*

Li et al., Fabrication of porous hollow silica nanoparticles and their applications in drug release control, J. Control. Release, 98 (2004) 245-254 (Li III).*

Ke et al., Solubilities of Salicylic Acid in Supercritical Carbon Dioxide with Ethanol Cosolvent, J. Supercrit. Fluids, 1996, 9, 82-87 (Ke).*

Dow, Methocel Food Gums, Product Brochure; accessed Dec. 19, 2014.*

Dow, Using Dow Excipients for Controlled Release of Drugs in Hydrophilic Matrix Systems, 2006; accessed Dec. 22, 2014.*

* cited by examiner

FORMULATION OF SILYMARIN WITH HIGH EFFICACY AND PROLONGED ACTION AND THE PREPARATION METHOD THEREOF

FIELD OF THE INVENTION

This invention relates to a high-efficacy, long-acting, slow-release drug formulation and its preparation method, and particularly to a high-efficacy, long-acting formulation of silymarin and its preparation method that enable silymarin to function 72 hours continuously in a slow-release mode.

BACKGROUND OF THE INVENTION

Silymarin (SLM) is a new flavonoid compound extracted from silybum marianum. It is a yellowish powder substance containing silybinin, isosilybinin, silydianin and silychristin. Amongst these components the content of silybinin is the highest and its activity is the highest as well. Silymarin presents a large variety of physiological effects, such as liver protection, blood lipid reduction, anti-oxidation, diabetes prevention, myocardial protection, anti-platelet aggregation and antineoplasm. [see: Flora K, Hahn M, Rahn H, et, al. "Milk Thistle (silybum marianum) for the Therapy of Liver Diseases." *Am J Gastroenterol* 93.13 (1998):139; Yan Yufeng & Yu Jiandong. "Chemical Composition of Silymarin Marianus and Recent Development of Its Pharmacological Research." *Chinese Pharmaceutical Affairs* 14.5 (2000): 335.] However, the bioavailability of silymarin remains considerably low due to its poor solubility in water. In recent years, the research on new dosage forms and preparation methods of silymarin focuses on increasing its oral bioavailability, for example, preparing silymarin in the form of lecithin complex, solid dispersion or cyclodextrin inclusion compound [see: Giacomellis S, Gallo D, Apollonio P, et, al. "Silybin and Its Bioavailable Phospholipid Complex (IdB 1016) Potentiate in vitro and in vivo the Activity of Cisplatin." *Life Sci* 70.12 (2002):1447; Li Fengqian, Hu Jinhong, Zhu Quangang, et, al. "Determination of total flavonoids in Silybinin Solid Dispersion." *Chinese Traditional and Herbal Drugs* 33.1 (2002): 31; Li Fengqian, Hu Jinhong, Wang Hui, et, al. "Solubilization and Lattice Changing Effect of PEG 6000 Solid Dispersion System on Poorly Soluble Silymarin." *Pharmaceutica Sinica* 37.4 (2002):294; Lirussi F, Beccarello A, Zanette G, et, al. "Silybin-beta-cyclodextrin in the Treatment of Patients with Diabetes Mellitus and Alcohol Liver Disease: Efficacy Study of a New Preparation of an Antioxidant Agent." *Diabets Nutr Metab* 15.4 (2003):222.].

Compared with other said methods, solid dispersion technique is more extensively utilized in virtue of its simple preparation procedure and outstanding solubilization effect [see: Deng Li, et, al. "Research on Preparation Methods and in vitro Dissolution of Silymarin Solid Dispersion." *Journal of the Second Military Medical University* 21.10 (2000):961; Wei Zhenping, Mao Shirui, Bi Dianzhou, et, al. "Dissolution Improvement of Cisapride by Solid Dispersion with HPMC," *Journal of Chinese Pharmaceutical Science* 13.4 (2004):254; Cui Fude, Yang Mingshi, Jiang Yanyan. "Design of Sustained-release Nitrendipine Microspheres Having Solid Dispersion Structure by Quasi-emulsion Solvent Diffusion Method." *Journal of Controlled Release* 97.3 (2003):375.]. When being prepared in the form of solid dispersion, the solubility and dissolution rate of the poorly soluble drug are enhanced, which consequently improve absorbability of the drug and increase its bioavailability. But such defects of the poorly soluble drug as frequent administrations and big difference between peak and trough concentrations remain unchanged. Controlled release preparation of drugs is being widely used in virtue of its less total amount and frequency of administration, which consequently avoids peak and trough phenomenon of plasma concentration, reduces toxic and side effects and improves patients' adaptability [see: Lee K, Nguyen T, Hanley T, et, al. "Nanostructure of Liquid Crystalline Matrix Determines in vitro Sustained Release and in vivo Oral Absorption Kenetics for Hydrophilic Model Drugs." *International Journal of Pharmaceutics* 365.1-2 (2009): 190; Wang Jiexin, Wang Zhihui, Chen Jianfeng, et, al. "Direct Encapsulation of Water-soluble Drug into Silica Microcapsules for Sustained Release Applications." *Materials Research Bulletin* 43.12 (2008): 3374.]. Therefore, the defects such as great fluctuation of plasma concentration and frequent administrations of the poorly soluble drug can be effectively avoided when the drug is prepared in slow-release form after having been solubilized.

In recent years, much attention has been attracted to the special structure and features of the mesoporous material. It refers to a type of material containing multiple pores with diameter between 2 to 50 nanometers. A mesoporous material can be disordered or ordered according to the structure of the mesopores. The ordered mesoporous material enjoys the following structural characteristics: 1. long-range structure being ordered; 2. pore size distribution being narrow and adjustable between 1.5 to 10 nanometers; 3. specific surface area reaching as high as 1000 $m^2/g$; 4. high porosity and 5. rich unsaturated radicals on its surface. When used as a drug carrier, the ordered mesoporous material presents the following advantages: 1. being nontoxic, nonphysioactive and biocompatible; 2. having evenly distributed, adjustable pore canals, within which its rich silanic radicals act as active sites for combining organic guest molecules; the drug molecules, through combining with these radicals, distribute within the canals evenly as well. Since the drug is absorbed within the ordered mesoporous material, it acts in a slow-release way; 3. protecting the integrity of molecular structure of the drug. Therefore, an ideal controlled release can be achieved for the hydrophobic drug when the mesoporous material is adopted as the controlled release carrier. The release effect varies in relation to the structure of the pore canal of the ordered mesoporous material.

On the basis of "triple release" mechanism comprising quick-release of the solid dispersion, regular slow-release of the hydrophilic gel matrix and the long-acting slow-release of the ordered mesoporous material, this invention is intended to prepare a 72-hour controlled release formulation of silymarin encompassing both quick-release and double slow-release, and presenting double pharmacokinetic effects of high-efficacy and long action.

DESCRIPTION OF THE INVENTION

Solid dispersion technique, ordered mesoporous nanoparticle technique and hydrophilic gel matrix technique are combinedly adopted in this invention in order to prepare a 72-hour controlled release, high-efficacy, long-acting formulation of silymarin characteristic of high bioavailability and smooth in vivo release.

The technical solution provided in this invention includes:

A high-efficacy, long-acting formulation of silymarin, comprising silymarin solid dispersion, silymarin-loaded silica nanoparticles, slow-release matrix material and release enhancer, wherein the mass ratio of these components is silymarin solid dispersion:silymarin-loaded silica nanoparticles:slow-release matrix material:release enhancer=1: 0.5~1.25:0.1~0.3:0.1~0.3; the drug loading rate of the said silymarin-loaded silica nanoparticles is 51.95%-52.87%; the said silymarin solid dispersion contains povidone K30, soybean lecithin and acrylic resin IV, wherein the mass ratio between silymarin and other medical accessories is silymarin: povidone K30:soybean lecithin:acrylic resin IV=1: 1~3:0.3~0.8:0.2~0.5.

The said high-efficacy, long-acting formulation of silymarin is prepared in the form of tablets or capsules.

A method for preparing the said high-efficacy, long-acting silymarin, comprising the following steps:

step 1. taking silymarin 1 g, povidone K30 1-3 g, soybean lecithin 0.3-0.8 g and acrylic resin IV 0.2-0.5 g and injecting in absolute ethyl alcohol 20-40 ml (70° C. water-bath can be adopted to accelerate dissolution if necessary); after the said materials having dissolved, treating the solution with 60° C. water-bath; then rotarily evaporating the solution at 90 rpm till almost dry, and then treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the silymarin solid dispersion is therefore obtained and ready for later use;

step 2. taking cyclohexane 20-80 ml, adding in nonyl phenol 10 (NP-10) 4-8 ml and mixing them together; adding in n-hexanol 1-3 ml, 25.6% ammonia water 1-3 ml and agitating for 1 hour at room temperature; slowly dropping in tetraethyl orthosilicate 3-5 ml and agitating for 24 hours at room temperature; adding in absolute ethyl alcohol 40-80 ml and treating with ultrasound for 1 hour; and then centrifugally separating at 15000 rpm for 15 min, washing the precipitate with distilled water three times; adding in some water, freezing and drying the substance in succession, and silica nanoparticles 8 g-32 g are therefore obtained;

taking the said silica nanoparticles 1 g, adding in 0.6 mol/L $Na_2CO_3$ solution 1000 ml, and then treating with ultrasound for 4-5 min under the condition of 60-70° C., 200 W; centrifugally separating the solution at 15000 rpm for 15 min and washing the precipitate with distilled water three times; adding in distilled water 10 ml, freezing and drying the substance in succession, and mesoporous silica nanoparticles are therefore obtained;

dissolving silymarin 2 g in absolute ethyl alcohol 10-20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and silymarin-loaded nanoparticles 2 g are therefore obtained, the drug loading rate of which is 51.95%~52.87%;

step 3. taking silymarin solid dispersion prepared in step 1 1 g, mixing it with hypromellose K4M 0.2-0.3 g and low-substituted hydroxypropyl cellulose (L-HPC) 0.1-0.2 g, and adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained;

step 4. taking silymarin solid dispersion prepared in step 1 1 g, mixing it with hypromellose K4M 0.1-0.2 g, low-substituted hydroxypropyl cellulose (L-HPC) 0.2-0.3 g, silymarin-loaded silica nanoparticles prepared in step 2 1.25-2.5 g and mixing them together; adding in some 70% syrup so that a certain soft substance is obtained, sieving the soft substance with 16 mesh and the wet granules so obtained are baked at 60° C. for 30 min, reshaping the granules with 16 mesh and the slow-release granules 2 are therefore obtained;

step 5. mixing the slow-release granules 1 prepared in step 3 and the slow-release granules 2 prepared in step 4 together and at the ratio of 1:2.75~1:4; tableting the mixed granules with the force around 40-60N and the high-efficacy, long-acting tablet of silymarin disclosed in this invention is obtained.

Adopting the said preparation method of the high-efficacy, long-acting formulation of silymarin, mixing the slow-release granules 1 prepared in step 3 and the slow-release granules 2 prepared in step 4 together at the ratio of 1:2.75~1:4; encapsulating the mixed granules and the high-efficacy, long-acting capsule of silymarin disclosed in this invention is obtained.

Beneficial Effects

1. This invention initiates a so-called "triple release" mechanism jointly realized by the quick-release of solid dispersion, the regular slow-release of hydrophilic gel matrix and the long-acting slow-release of mesoporous silica nanoparticles; based on the "double release" method comprising the quick-release technique and the regular slow-release technique, this mechanism fully utilizes the long-acting slow-release characteristic of the drug-loaded ordered mesoporous material, an advantage resulting from its high absorption due to its high specific surface area and big pore volume; taking ordered mesoporous silica nanoparticles as carrier material and integrating solid dispersion technique, ordered mesoporous nanoparticles technique and hydrorphilic gel matrix technique together, a new formulation of silymarin that starts with quick-release, then regular slow-release, and long-acting slow-release at last is prepared, namely, the formulation encompasses quick-release and double slow-release simultaneously. Compared with the existing formulations through in vivo testing in Beagle dogs, the half life of the high-efficacy, long-acting formulation of silymarin disclosed in this invention is 2.3 times longer while the mean residence time (MRT) of which is 7.94 times longer; the in vivo pharmacokinetic testing in Beagle dogs also indicates that this formulation of silymarin presents a smoother concentration-time curve and reaches a continuous release for 72 hours.

2. This invention combines solid dispersion technique and nanotechnique together; on the one hand, soybean lecithin is added in during the preparation of silymarin solid dispersion, which consequently enhances physical absorption of silymarin; on the other hand, the utilization of nanoparticles technique remarkably enhances the speed and extent of the physical absorption of silymarin, which is contributive to higher bioavailability of the long-acting, slow-release formulation of silymarin as well. Therefore, the silymarin formulation disclosed in this invention is not only a long-acting, slow-release one, but also a formulation of high-efficacy, that is to say, it is a formulation simultaneously presents the double advantages of high-efficacy and long-action. Compared with the control formulation through in vivo pharmacokinetic testing in Beagle dogs, the relative bioavailability of the long-acting, slow-release formulation of silymarin prepared with the method disclosed in this invention is 3017%. In addition, the method disclosed in this invention can be utilized in developing sophisticated, high-efficacy and long-acting drug formulations that need to be administered only once three days.

3. Silica is biological compatible, nontoxic and extensively available; the silica nanoparticles prepared with the method disclosed in this invention have such advantages as simple preparation method, no requirement of special devices, fewer influencing factors during preparation, and higher repeatibility.

DETAILED DESCRIPTION OF PREFERRED EMBODIMENTS

Figure 1:
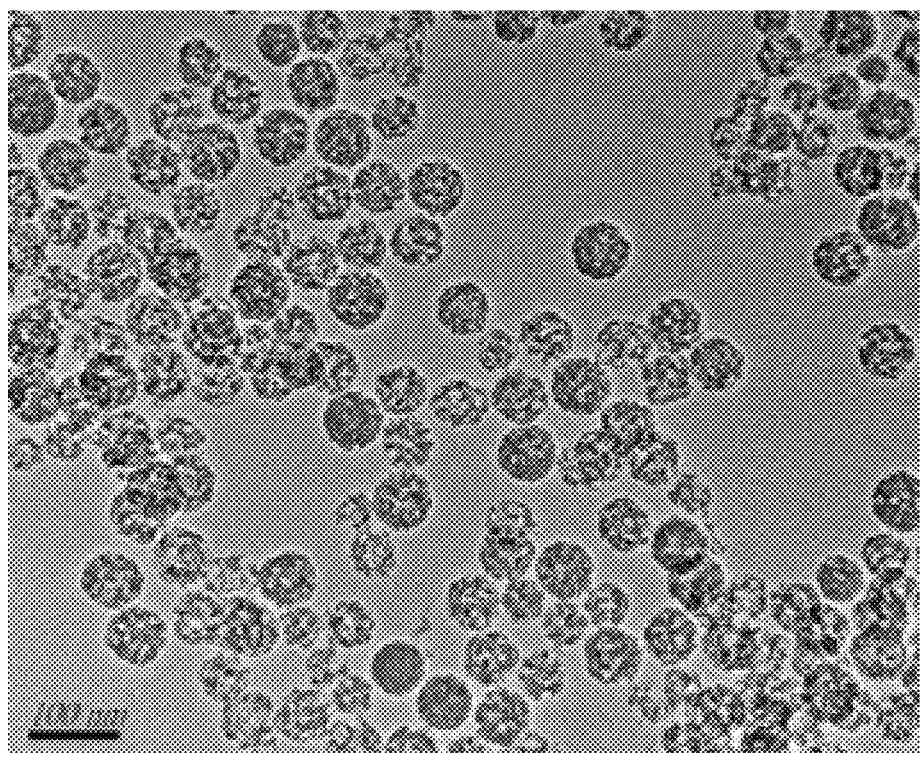
FIG. 1 is a TEM image of the mesoporous silica nanoparticles prepared in this invention.

The materials and devices required for the following embodiments include:

experiment materials: povidone K30 (Shanghai Shengpu New Materials Co., Ltd.); soybean lecithin (Shanghai Taiwei Pharmaceutical Co., Ltd.); acrylic resin IV (Huainan Shanhe Medical Accessories Co., Ltd.); tetraethyl orthosilicate (Chemical Reagent Co., Ltd. of China National Pharmaceutical Group); hypromellose K4M (Shanghai Colorcon Coating Technology Co., Ltd.); L-HPC (Shanghai Colorcon Coating Technology Co., Ltd); NP-10 (Shanghai Jiafang Trade Co., Ltd.).

experiment devices: rotary evaporator (Heidolph, Germany); H66025 ultrasonic cleaner (Wuxi Ultrasonic Devices Factory); ADP single punch tablet machine (Shanghai Tianxiang Pharmaceutical machinery Co., Ltd.).

Embodiment I

Taking silymarin 1 g, povidone K30 1 g, soybean lecithin 0.2 g and acrylic resin IV 0.1 and injecting in absolute ethyl alcohol 20 (70° C. water-bath can be adopted to accelerate dissolution if necessary); after the said materials having dissolved, treating the solution with 60° C. water-bath, then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 30 ml, adding in nonyl phenol 10 (NP-10) 4 ml and mixing them together; adding in n-hexanol 1 ml, 25.6% ammonia water 1 ml and agitating for 1 hour at room temperature; slowly dropping in tetraethyl orthosilicate 3 ml and agitating for 24 hours at room temperature; adding in absolute ethyl alcohol 40 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Figure 2:
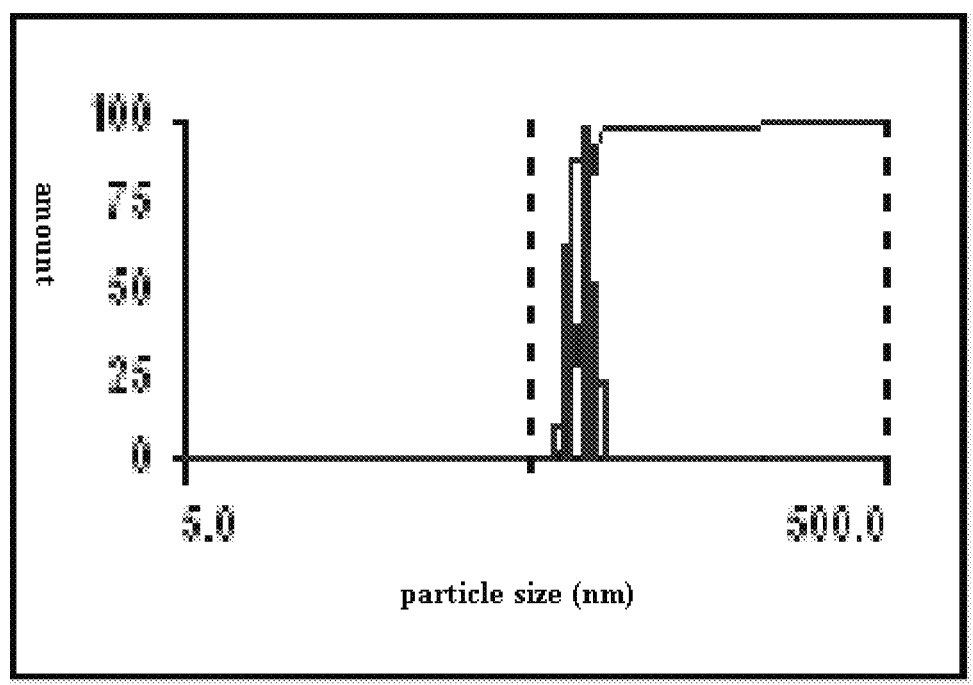
FIG. 2 is the particle size distribution graph of the mesoporous silica nanoparticles prepared in this invention.
Figure 3:
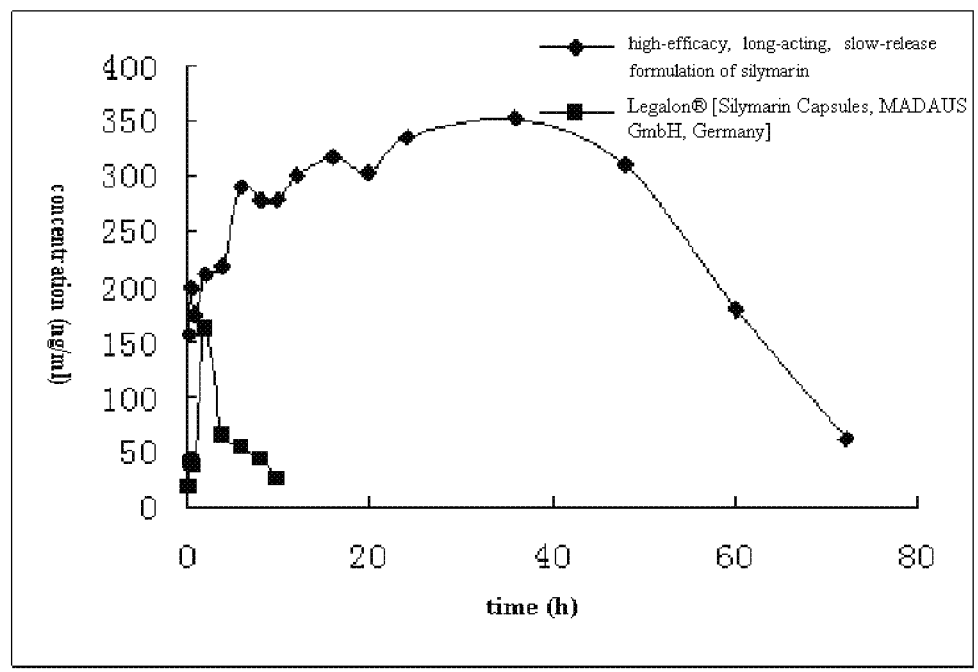
FIG. 3 is the concentration-time curve of the high-efficacy, long-acting, slow-release formulation of silymarin disclosed in this invention when tested in vivo in Beagle dogs.

Taking the said silica nanoparticles 2 g, adding in 0.6 mol/L $Na_2CO_3$ solution 2000 ml, and treating with ultrasound for 4 min under the condition of 60° C., 200 W; and then centrifugally separating at 15000 rpm for 15 min and washing the precipitate with distilled water three times; adding in distilled water 10 ml, freezing and drying the substance in succession, and mesoporous silica nanoparticles are therefore obtained (see: FIG. 1 and FIG. 2).

Dissolving silymarin 3 g in absolute ethyl alcohol 20 ml, soaking mesoporous silica nanoparticles 1.5 g in the solution for 24 hours, and then centrifugally separating at 15000 rpm for 15 min and washing the precipitate with absolute ethyl alcohol three times; adding in distilled water 10 ml, freezing and drying the substance in succession, and silymarin-loaded nanoparticles are therefore obtained.

Taking silymarin solid dispersion 1 g, mixing it with hypromellose K4M 0.2 g and L-HPC 0.2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking silymarin solid dispersion 1.8 g, mixing it with hypromellose K4M 0.36 g, L-HPC 0.4 g and silymarin-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 1:2; and then tableting the mixed granules with the force around 40-60N; the high-efficacy, long-acting tablet of silymarin is therefore obtained.

Embodiment II

Taking silymarin 1 g, povidone K30 3 g, soybean lecithin 0.8 g and acrylic resin IV 0.5 g and injecting in absolute ethyl alcohol 40 ml (70° C. water-bath can be adopted to accelerate dissolution if necessary); after the said materials having dissolved, treating the solution with 60° C. water-bath; then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 80 ml, adding in nonyl phenol 10 (NP-10) 8 ml and mixing them together; adding in n-hexanol 3 ml, 25.6% ammonia water 3 ml and agitating for 1 hour at room temperature; slowly dropping in tetraethyl orthosilicate 5 ml and agitating for 24 hours at room temperature; adding in absolute ethyl alcohol 80 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 3 g, adding in 0.6 mol/L $Na_2CO_3$ solution 3000 ml, and treating with ultrasound for 4 min under the condition of 60° C., 200 W; and then centrifugally separating at 15000 rpm for 15 min and washing the precipitate with distilled water three times; adding in distilled water 10 ml, freezing and drying the substance in succession, and mesoporous silica nanoparticles are therefore obtained.

Dissolving silymarin 3 g in absolute ethyl alcohol 20 ml, soaking mesoporous silica nanoparticles 1.5 g in the solution for 24 hours, and then centrifugally separating at 15000 rpm for 15 min and washing the precipitate with absolute ethyl alcohol three times; adding in distilled water 10 ml, freezing and drying the substance in succession, and silymarin-loaded nanoparticles are therefore obtained.

Taking silymarin solid dispersion 1.8 g, mixing it with hypromellose K4M 0.4 g and L-HPC 0.4 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking silymarin solid dispersion 1.8 g, mixing it with hypromellose K4M 0.36 g, L-HPC 0.4 g and silymarin-loaded silica nanoparticles 3 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 2:3; and then encapsulating the mixed granules so that the high-efficacy, long-acting capsule of silymarin is obtained.

Embodiment III

Taking silymarin 1 g, povidone K30 1.2 g, soybean lecithin 0.4 g and acrylic resin IV 0.3 g and injecting in absolute ethyl alcohol 25 ml (70° C. water-bath can be adopted to accelerate dissolution if necessary); after the said materials having dissolved, treating the solution with 60□ water-bath; then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 30 ml, adding in nonyl phenol 10 (NP-10) 5 ml and mixing them together; adding in n-hexanol 1.2 ml, 25.6% ammonia water 1.5 ml and agitating for 1 hour at room temperature; slowly dropping in tetraethyl orthosilicate 3.5 ml and agitating for 24 hours at room temperature; adding in absolute ethyl alcohol 50 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 1 g, adding in 0.6 mol/L $Na_2CO_3$ solution 1000 ml, treating with ultrasound for 4.5 min under the condition of 65° C., 200 W, and then centrifugally separating at 15000 rpm for 15 min and washing the precipitate with distilled water three times; adding in distilled water 10 ml, freezing and drying the substance in succession, and mesoporous silica hollow nanoparticles are therefore obtained.

Dissolving silymarin 2 g in absolute ethyl alcohol 20 ml, soaking mesoporous silica hollow nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and silymarin-loaded nanoparticles are therefore obtained.

Taking silymarin solid dispersion 1 g, mixing it with hypromellose K4M 0.2 g and L-HPC 0.2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking silymarin solid dispersion 1 g, mixing it with hypromellose K4M 0.1 g, L-HPC 0.3 g and silymarin-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 2:3; and then tableting the mixed granules with the force around 40-60N; the high-efficacy, long-acting tablet of silybinin is therefore obtained.

Embodiment IV

Taking silymarin 1 g, povidone K30 1.5 g, soybean lecithin 0.5 g and acrylic resin IV 0.4 g and injecting in absolute ethyl alcohol 30 ml (70□ water-bath can be adopted to accelerate dissolution if necessary); after the said materials having dissolved, treating the solution with 60° C. water-bath; then rotarily evaporating the solution at 90 rpm till almost dry, and treating the substance with 70° C. water-bath till the solvent completely evaporates; putting the substance so obtained into a −20° C. freezer for 2 hours and then into a 60° C. drying oven for 12 hours; comminuting the substance and sieving it with 80 mesh; the solid dispersion is therefore obtained and ready for later use.

Taking cyclohexane 50 ml, adding in nonyl phenol 10 (NP-10) 6 ml and mixing them together; adding in n-hexanol 2.2 ml, 25.6% ammonia water 1.8 ml and agitating for 1 hour at room temperature; slowly dropping in tetraethyl orthosilicate 4.2 ml and agitating for 24 hours at room temperature; adding in absolute ethyl alcohol 60 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 1 g, adding in 0.6 mol/L $Na_2CO_3$ solution 1000 ml, treating with ultrasound for 4.5 min under the condition of 65° C., 200 W, and then centrifugally separating at 15000 rpm for 15 min and washing the precipitate with distilled water three times; adding in distilled water 10 ml, freezing and drying the substance in succession, and mesoporous silica hollow nanoparticles are therefore obtained.

Dissolving silymarin 2 g in absolute ethyl alcohol 20 ml, soaking mesoporous silica nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and silymarin-loaded nanoparticles are therefore obtained.

Taking silymarin solid dispersion 1 g, mixing it with hypromellose K4M 0.22 g and L-HPC 0.22 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking silymarin solid dispersion 1 g, mixing it with hypromellose K4M 0.15 g, L-HPC 0.25 g and silymarin-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 2:3; and then tableting the mixed granules with the force around 40-60N; the high-efficacy, long-acting tablet of silybinin is therefore obtained.

Embodiment V

Taking silymarin 1 g, povidone K30 2.5 g, soybean lecithin 0.7 g and acrylic resin IV 0.4 g and injecting in absolute ethyl alcohol 40 ml (70° C. water-bath can be adopted to accelerate dissolution if necessary); after the said materials having dissolved, treating the solution with 60° C. water-bath; then rotarily evaporating the solution at 90 rpm till almost dry, and treating the substance with 70° C. water-bath till the solvent completely evaporates; putting the substance so obtained into a –20° C. freezer for 2 hours and then into a 60° C. drying oven for 12 hours; comminuting the substance and sieving it with 80 mesh; the solid dispersion is therefore obtained and ready for later use.

Taking cyclohexane 70 ml, adding in nonyl phenol 10 (NP-10) 6 ml and mixing them together; adding in n-hexanol 1 ml, 25.6% ammonia water 1.5 ml and agitating for 1 hour at room temperature; slowly dropping in tetraethyl orthosilicate 6 ml and agitating for 24 hours at room temperature; adding in absolute ethyl alcohol 60 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 2 g, adding in 0.6 mol/L $Na_2CO_3$ solution 2000 ml, treating with ultrasound for 5 min under the condition of 70° C., 200 W, and then centrifugally separating at 15000 rpm for 15 min and washing the precipitate with distilled water three times; adding in distilled water 10 ml, freezing and drying the substance in succession, and mesoporous silica hollow nanoparticles are therefore obtained.

Dissolving silymarin 2 g in absolute ethyl alcohol 15 ml, soaking mesoporous silica hollow nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and silymarin-loaded nanoparticles are therefore obtained.

Taking silymarin solid dispersion 1.2 g, mixing it with hypromellose K4M 0.3 g and L-HPC 0.3 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking silymarin solid dispersion 1.8 g, mixing it with hypromellose K4M 0.36 g, L-HPC 0.32 g and silymarin-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 1:1; and then tableting the mixed granules with the force around 40-60N; the high-efficacy, long-acting tablet of silybinin is therefore obtained.

Embodiment VI

Taking silymarin 1 g, povidone K30 2 g, soybean lecithin 0.8 g and acrylic resin IV 0.2 g and injecting in absolute ethyl alcohol 40 ml (70° C. water-bath can be adopted to accelerate dissolution if necessary); after the said materials having dissolved, treating the solution with 60° C. water-bath; then rotarily evaporating the solution at 90 rpm till almost dry, and treating the substance with 70° C. water-bath till the solvent completely evaporates; putting the substance so obtained into a –20° C. freezer for 2 hours and then into a 60° C. drying oven for 12 hours; comminuting the substance and sieving it with 80 mesh; the solid dispersion is therefore obtained and ready for later use.

Taking cyclohexane 60 ml, adding in nonyl phenol 10 (NP-10) 5 ml and mixing them together; adding in n-hexanol 1 ml, 25.6% ammonia water 1.5 ml and agitating for 1 hour at room temperature; slowly dropping in tetraethyl orthosilicate 5.5 ml and agitating for 24 hours at room temperature; adding in absolute ethyl alcohol 70 ml and treating with ultrasound for 1 hour; and then centrifugally separating at 15000 rpm for 15 min and washing the precipitate with distilled water three times; adding in some water, freezing and drying the substance in succession, and the powder of silica nanoparticles is therefore obtained.

Taking the said silica nanoparticles 2 g, adding in 0.6 mol/L $Na_2CO_3$ solution 2000 ml, treating with ultrasound for 5 min under the condition of 70° C., 200 W, and then centrifugally separating at 15000 rpm for 15 min and washing the precipitate with distilled water three times; adding in distilled water 10 ml, freezing and drying the substance in succession, and mesoporous silica hollow nanoparticles are therefore obtained.

Dissolving silymarin 2 g in absolute ethyl alcohol 15 ml, soaking mesoporous silica hollow nanoparticles 1 g in the solution for 24 hours, and then centrifugally separating at 15000 rpm for 15 min and washing the precipitate with absolute ethyl alcohol three times; adding in distilled water 10 ml, freezing and drying the substance in succession, and silymarin-loaded nanoparticles are therefore obtained.

Taking silymarin solid dispersion 1.4 g, mixing it with hypromellose K4M 0.3 g and L-HPC 0.3 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 1 are therefore obtained.

Taking silymarin solid dispersion 2.1 g, mixing it with hypromellose K4M 0.42 g, L-HPC 0.48 g and silymarin-loaded silica nanoparticles 2 g, and then adding in some 70% syrup so that a certain soft substance is obtained; sieving the soft substance with 16 mesh and the wet granules so obtained are baked at 60° C. for 30 min, reshaping the granules with 16 mesh and the slow-release granules 2 are therefore obtained.

Mixing the slow-release granules 1 and the slow-release granules 2 at the ratio of 1:1; and then tableting the mixed granules with the force around 40-60N; the high-efficacy, long-acting tablet of silybinin is therefore obtained.

What is claimed is:
1. A formulation of silymarin, comprising:
  a silymarin solid dispersion, silymarin-loaded silica nanoparticles, a slow-release matrix material and a release enhancer, wherein a mass ratio of the silymarin solid dispersion:the silymarin-loaded silica nanoparticles:the slow-release matrix material:the release enhancer is 1:0.5-1.25:0.1-0.3:0.1-0.3;
  wherein the silica nanoparticles are a mesoporous material including a plurality of pores having a diameter of 1.5 nm to 50 nm;
  wherein the silymarin solid dispersion contains povidone K30, soybean lecithin, acrylic resin IV, wherein a mass ratio of silymarin:povidone K30:soybean lecithin: acrylic resin IV is 1:1-3:0.3-0.8:0.2-0.5.

2. The formulation of silymarin as is defined in claim 1, wherein the formulation is prepared in the form of at least one of a tablet and a capsule.

3. The formulation of silymarin as is defined in claim 1 wherein silymarin is controllably released for approximately 72 hours.

4. A method for preparing a formulation of silymarin, comprising the following steps:
providing a silymarin solid dispersion;
preparing a mixture of cyclohexane, nonyl phenol 10 (NP-10), n-hexanol and ammonia water;
dropping in tetraethyl orthosilicate directly into the mixture;
treating the mixture with ultrasound and centrifugally separating the mixture to obtain silica nanoparticles;
adding a $Na_2CO_3$ solution to the silica nanoparticles;
treating the $Na_2CO_3$ solution added to the silica nanoparticles with ultrasound to obtain mesoporous silica nanoparticles with a porous diameter between 1.5 nm to 50 nm;
soaking the mesoporous silica nanoparticles in an absolute ethyl alcohol solution of silymarin to obtain silymarin-loaded silica nanoparticles;
mixing a first portion of the silymarin solid dispersion with hypromellose that has a viscosity of 4000 cPs in a 2% aqueous solution, and low-substituted hydroxypropyl cellulose (L-HPC), and dividing the mixture into (a) a first portion comprising the silymarin solid dispersion, hypromellose that has a viscosity of 4000 cPs in a 2% aqueous solution, and L-HPC, and (b) a second portion comprising the silymarin solid dispersion, hypromellose that has a viscosity of 4000 cPs in a 2% aqueous solution, and L-HPC;
sieving the mixture of (a) the first portion comprising the silymarin solid dispersion, hypromellose that has a viscosity of 4000 cPs in a 2% aqueous solution, and low-substituted hydroxypropyl cellulose (L-HPC) to obtain a first set of slow release granules;
mixing (b) the second portion comprising the silymarin solid dispersion, with hypromellose that has a viscosity of 4000 cPs in a 2% aqueous solution, and low-substituted hydroxypropyl cellulose (L-HPC) with the silymarin-loaded silica nanoparticles to obtain a second set of slow release granules; and
mixing the first set of slow release granules and the second set of slow release granules together at a ratio of 1:1 to 1:4.

5. A method for preparing the formulation of silymarin as is defined in claim 4, further comprising the step of tableting or encapsulating the mixture of the first set of slow release granules and the second set of slow release granules.

6. The formulation of claim 1, wherein the silica nanoparticles have a specific surface area as high as 1000 $m^2/g$.

7. The formulation of claim 1, wherein a bioavailability of the formulation of silymarin is 383%.

8. A formulation of silymarin, consisting essentially of:
a silymarin solid dispersion, silymarin-loaded silica nanoparticles, a slow-release matrix material and a release enhancer, wherein a mass ratio of the silymarin solid dispersion:the silymarin-loaded silica nanoparticles:the slow-release matrix material:the release enhancer is 1:0.5-1.25:0.1-0.3:0.1-0.3, wherein the silica nanoparticles are a mesoporous material including a plurality of pores having a diameter of 1.5 nm to 50 nm, wherein the silymarin solid dispersion contains povidone K30, soybean lecithin, acrylic resin IV, wherein a mass ratio of silymarin:povidone K30:soybean lecithin:acrylic resin IV is 1:1-3:0.3-0.8:0.2-0.5.

9. The formulation of claim 8, wherein the silymarin loaded silica nanoparticles have a silymarin loading between 51.29% to 51.77%.

* * * * *